(12) United States Patent
Tahmasebi Maraghoosh et al.

(10) Patent No.: US 12,300,391 B2
(45) Date of Patent: May 13, 2025

(54) SELECTING A TREATMENT FOR A PATIENT

(71) Applicant: KONINKLIJKE PHILIPS N.V., Eindhoven (NL)

(72) Inventors: Amir Mohammad Tahmasebi Maraghoosh, Arlington, MA (US); Reza Sharifi Sedeh, Malden, MA (US); Eran Rubens, Palo Alto, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 796 days.

(21) Appl. No.: 17/272,466

(22) PCT Filed: Aug. 27, 2019

(86) PCT No.: PCT/EP2019/072737
§ 371 (c)(1),
(2) Date: Mar. 1, 2021

(87) PCT Pub. No.: WO2020/043673
PCT Pub. Date: Mar. 5, 2020

(65) Prior Publication Data
US 2021/0327596 A1 Oct. 21, 2021

Related U.S. Application Data

(60) Provisional application No. 62/723,603, filed on Aug. 28, 2018.

(51) Int. Cl.
*G16H 70/20* (2018.01)
*G16H 10/60* (2018.01)
(Continued)

(52) U.S. Cl.
CPC ............. *G16H 70/20* (2018.01); *G16H 10/60* (2018.01); *G16H 20/00* (2018.01); *G16H 40/20* (2018.01)

(58) Field of Classification Search
CPC ........ G16H 70/20; G16H 10/60; G16H 20/00; G16H 40/20
See application file for complete search history.

(56) References Cited

U.S. PATENT DOCUMENTS

2008/0281639 A1   11/2008   Quinn et al.
2009/0018867 A1*  1/2009    Reiner ................ G06F 3/04883
                                                                705/2

(Continued)

FOREIGN PATENT DOCUMENTS

WO      2015031296 A1     3/2015
WO      2017064600 A1     4/2017
WO   WO-2017077501 A1 *   5/2017     ......... G06F 17/2705

OTHER PUBLICATIONS

International Search Report and Written Opinion for International Application No. PCT/EP2019/072737, filed Aug. 27, 2019, 16 pages.

*Primary Examiner* — Mohammad Ali
*Assistant Examiner* — Vincent W Chang (57) ABSTRACT

Methods and systems for selecting a treatment for a patient. The system extracts an incidental finding from a record associated with a patient and an associated follow-up recommendation. The system then determines whether any inconsistencies exist between the follow-up recommendation from the report and a follow-up recommendation prescribed by institutional or administrative guidelines. Any inconsistencies may then be resolved to guarantee an appropriate workflow for patient care.

22 Claims, 3 Drawing Sheets

(51) Int. Cl.
*G16H 20/00* (2018.01)
*G16H 40/20* (2018.01)

(56) References Cited

U.S. PATENT DOCUMENTS

| | | |
|---|---|---|
| 2013/0262364 A1 | 10/2013 | Verbeek |
| 2013/0311472 A1* | 11/2013 | Cohen-Solal .......... G16H 30/20 |
| | | 707/737 |
| 2014/0303988 A1* | 10/2014 | Maneri .................. G16H 50/20 |
| | | 705/2 |
| 2014/0365232 A1 | 12/2014 | Sadeghi |
| 2014/0365239 A1 | 12/2014 | Sadeghi |
| 2015/0149215 A1* | 5/2015 | Qian ..................... G06F 16/335 |
| | | 705/3 |
| 2017/0293734 A1 | 10/2017 | Potter et al. |
| 2019/0272919 A1* | 9/2019 | Frandsen ............... G16H 10/40 |
| 2021/0142480 A1* | 5/2021 | Thomson ............... G16H 50/20 |

* cited by examiner

| Guidlines from the Fleischner society ||
|---|---|
| Low-risk patients | High-risk patients |
| < 4 mm   No futher investigation | < 4 mm   CT at 12 months |
| 4-6 mm   CT at 12 months | 4-6 mm   CT at 6-12-18-24 months |
| 6-6 mm   CT at 6-12-18-24 months | 6-6 mm   CT at 3-6-9-12-24 months |
| > 8 mm   CT at 6-12-18-24 months | > 8 mm   CT at 3-6-9-12-24 months |
| contrast-enhanced CT<br>PET and/or biopsy | contrast-enhanced CT<br>PET and/or biopsy |

FIG. 3

SELECTING A TREATMENT FOR A PATIENT

RELATED APPLICATIONS

This application is the U.S. National Phase application under 35 U.S.C. § 371 of International Application No. PCT/EP2019/072737, filed on Aug. 27, 2019, which claims the benefit and priority to Provisional Application No. 62/723,603, filed Aug. 28, 2018, which is incorporated by reference in its entirety.

TECHNICAL FIELD

Embodiments described herein generally relate to systems and methods for selecting a treatment for a patient and, more particularly but not exclusively, to systems and methods for selecting a treatment for a patient based on follow-up recommendations to incidental findings.

BACKGROUND

During healthcare examinations, clinicians often encounter a finding that is not related to the original reason for the examination. This type of finding is known as an "incidental finding."

There are generally well-established guidelines that instruct clinicians how to handle incidental findings. For example, the American College of Radiology (ACR) or the clinical management team from a specific healthcare institution may each provide their own guidelines for dealing with incidental findings from a radiology examination.

Depending on the significance of the incidental finding, it may be important to provide a clear follow-up recommendation and for a clinician to pursue the recommended course of action. Failure to act on the follow-up recommendation may result in severe health concerns for the patient. In fact, it has been shown that in 30% of cases in which an incidental finding is made, no follow-up action is taken.

A need exists, therefore, for methods and systems that can provide accurate and appropriate follow-up recommendations for treating a patient.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

According to one aspect, embodiments relate to a method for selecting a treatment for a patient. The method includes extracting, using a processor executing instructions stored on a memory, at least one incidental finding from a record associated with the patient; extracting, using the processor, at least one first follow-up recommendation from the record; associating a first follow-up recommendation with a first incidental finding; obtaining, using an interface, a second follow-up recommendation from a third party-defined policy; determining, using the processor, whether any inconsistencies exist between the first follow-up recommendation and the second follow-up recommendation; presenting, using a user interface, a determination of whether any inconsistencies exist between the first follow-up recommendation and the second follow-up recommendation; receiving, using the user interface, user feedback as to which recommendation is to be used to resolve any determined inconsistencies; and updating, using the processor, a clinical care workflow based at least on the received user feedback.

In some embodiments, the third party is at least one of a healthcare institution and an administrative body.

In some embodiments, the method further includes receiving, using the user interface, a resolution upon the processor determining an inconsistency exists between the first follow-up recommendation and the second follow-up recommendation.

In some embodiments, the at least one incidental finding relates to a finding of a radiology examination.

In some embodiments, extracting the at least one incidental finding includes: identifying the at least one incidental finding in a medical examination report; and confirming that the at least one incidental finding is not a prior finding by analyzing longitudinal data associated with the patient.

In some embodiments, the method further includes extracting at least one patient feature from an electronic health record, wherein the at least one patient feature is required by the third party-defined policy, wherein the second follow-up recommendation is based on the at least one extracted patient feature.

In some embodiments, associating the first follow-up recommendation with the first incidental finding includes using at least one of a keyword matching approach, a model trained on paired training data, and existing guidelines specifying a required incidental finding for a given follow-up recommendation.

According to another aspect, embodiments relate to a system for selecting a treatment for a patient. The system includes an interface for receiving a record associated with the patient; and a processor executing instructions stored on a memory to extract at least one incidental finding from the record associated with the patient; extract at least one first follow-up recommendation from the record; associate the at least one first follow-up recommendation with the at least one incidental finding; obtain at least one second follow-up recommendation from a third party-defined policy; determine whether any inconsistencies exist between the at least one first follow-up recommendation and the at least one second follow-up recommendation; present, using a user interface, a determination of whether any inconsistencies exist between the at least one first follow-up recommendation and the at least one second follow-up recommendation; receive, using the user interface, user feedback as to which recommendation is to be used to resolve any determined inconsistencies; and update a clinical care workflow based at least on the received user feedback.

In some embodiments, the third party is at least one of a healthcare institution and an administrative body.

In some embodiments, the user interface is further configured to receive a resolution upon the processor determining an inconsistency exists between the at least one first follow-up recommendation and the at least one second follow-up recommendation.

In some embodiments, the at least one incidental finding relates to a finding of a radiology examination.

In some embodiments, the processor is configured to extract the at least one incidental finding by identifying the at least one incidental finding in a medical examination report; and confirming that the at least one incidental finding is not a prior finding by analyzing longitudinal data associated with the patient.

In some embodiments the processor is further configured to extract at least one patient feature from an electronic health record, wherein the at least one patient feature is required by the third party-defined policy, wherein the second follow-up recommendation is based on the at least one extracted patient feature.

In some embodiments, the processor associates the at least one first follow-up recommendation with the at least one incidental finding using at least one of a keyword matching approach, a model trained on paired training data, and existing guidelines specifying a required incidental finding for a given follow-up recommendation.

According to yet another aspect, embodiments relate to a non-transitory computer-readable medium containing computer executable instructions for performing a method for selecting a treatment for a patient. The computer-readable medium includes computer-executable instructions for extracting, using a processor executing instructions stored on a memory, at least one incidental finding from a record associated with the patient; computer-executable instructions for extracting, using the processor, at least one first follow-up recommendation from the record; computer-executable instructions for associating the at least one first follow-up recommendation with the at least one incidental finding; computer-executable instructions for obtaining, using an interface, at least one second follow-up recommendation from a third party-defined policy; computer-executable instructions for determining, using the processor, whether any inconsistencies exist between the at least one first follow-up recommendation and the at least one second follow-up recommendation; computer-executable instructions for presenting, using a user interface, a determination of whether any inconsistencies exist between the at least one first follow-up recommendation and the at least one second follow-up recommendation; computer-executable instructions for receiving, using the user interface, user feedback as to which recommendation is to be used to resolve any determined inconsistencies; and computer-executable instructions for updating, using the processor, a clinical care workflow based at least on the received user feedback.

BRIEF DESCRIPTION OF DRAWINGS

Non-limiting and non-exhaustive embodiments of the embodiments herein are described with reference to the following figures, wherein like reference numerals refer to like parts throughout the various views unless otherwise specified.

DETAILED DESCRIPTION

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment. The appearances of the phrase "in some embodiments" in various places in the specification are not necessarily all referring to the same embodiments.

Some portions of the description that follow are presented in terms of symbolic representations of operations on non-transient signals stored within a computer memory. These descriptions and representations are used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may comprise a general-purpose computer selectively activated or reconfigured by a computer program stored in the computer or by using some cloud-based solution. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

Medical personnel (for simplicity, "clinicians") frequently are tasked with reviewing imagery and other data relating to a patient's health as part of treatment. As mentioned previously, oftentimes clinicians encounter a finding that does not relate to the original reason an examination was conducted. Even if these findings (i.e., incidental findings) do not relate to the reason the examination was conducted, they nonetheless may have a significant impact on the patient's health.

Oftentimes, however, incidental findings do not result in a follow-up recommendation and/or further treatment. This can ultimately lead the patient to go untreated and may further lead to severe health consequences. It is therefore important to provide an automated way to ensure that proper care and attention is provided to incidental findings and the particular ailment(s) associated with the incidental finding.

Incidental findings may be common in radiology examinations. There may be three different scenarios related to incidental findings encountered during a radiology examination. In the first scenario, the radiologist may observe the incidental finding and provide a recommendation (e.g., by entering a note of the recommended follow-up in the patient's health record) that matches guidelines set by the ACR or some other administrative body.

In a second scenario, a radiologist may observe the incidental finding and provide a follow-up recommendation. However, the provided follow-up recommendation does not match the ACR guidelines or guidelines by some institution or administrative body.

In a third scenario, the radiologist may observe an incidental finding but does not provide a follow-up recommendation. For example, the radiologist may not think the incidental finding is significant enough to warrant a follow-up recommendation or the radiologist may ultimately forget to provide a follow-up recommendation. In this case, the particular ailment associated with the incidental finding may go untreated as the clinician did not provide any follow-up recommendation and the patient is likely unaware of the incidental finding or any associated complications.

Figure 1:
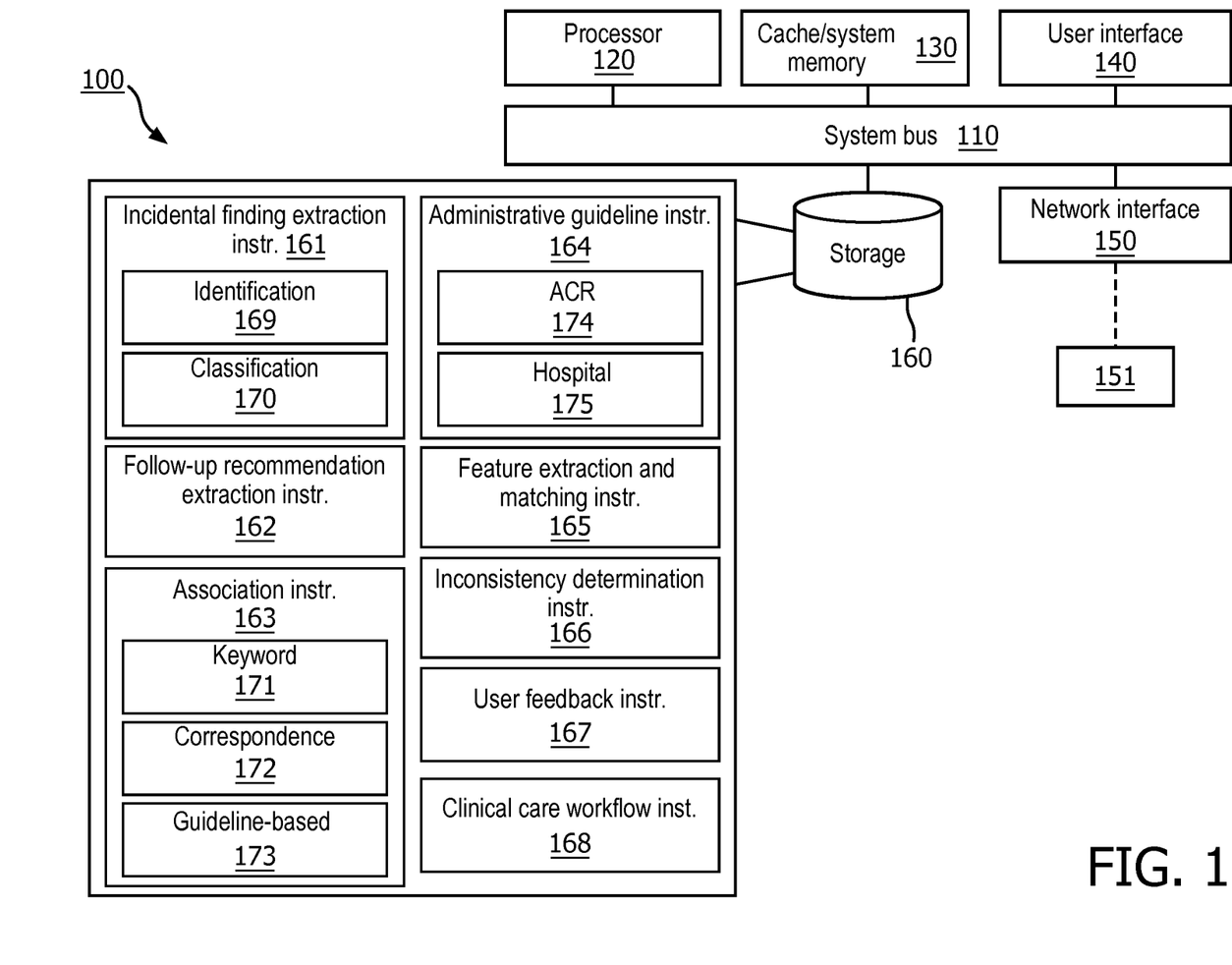
FIG. 1 illustrates a system for selecting a treatment for a patient in accordance with one embodiment.

The systems and methods described herein provide automatic and novel ways to deal with these scenarios to guarantee an appropriate workflow for patient care. FIG. 1 illustrates a system 100 for selecting a treatment for a patient in accordance with one embodiment.

The system 100 may include a processor 120, memory 130, a user interface 140, a network interface 150, and storage 160 interconnected via one or more system buses 110. It will be understood that FIG. 1 constitutes, in some respects, an abstraction and that the actual organization of the system 100 and the components thereof may differ from what is illustrated.

The processor 120 may be any hardware device capable of executing instructions stored on memory 130 or storage 160 or otherwise capable of processing data. As such, the processor 120 may include a microprocessor, field programmable gate array (FPGA), application-specific integrated circuit (ASIC), or other similar device(s).

In some embodiments, such as those relying on one or more ASICs, the functionality described as being provided in part via software may instead be configured into the design of the ASICs and, as such, the associated software may be omitted. The processor 120 may be configured as part of a user device on which the user interface 140 executes or may be located at some remote location.

The memory 130 may include various memories such as, for example L1, L2, or L3 cache or system memory. As such, the memory 130 may include static random access memory (SRAM), dynamic RAM (DRAM), flash memory, read only memory (ROM), or other similar memory devices. The exact configuration of the memory 130 may vary as long as instructions for selecting a treatment for a patient can be executed.

The user interface 140 may execute on one or more devices for enabling communication with a user such as a clinician or other type of medical personnel. For example, the user interface 140 may include a display, a mouse, and a keyboard for receiving user commands. In some embodiments, the user interface 140 may include a command line interface or graphical user interface that may be presented to a remote terminal via the network interface 150.

The user interface 140 may execute on a user device such as a PC, laptop, tablet, mobile device, smartwatch, or the like. The exact configuration of the user interface 140 and the device on which it executes may vary as along as the features of various embodiments described herein may be accomplished. The user interface 140 may enable a clinician to view imagery related to a medical examination, input notes related to an examination, view notes related to an examination, provide follow-up recommendations to incidental findings, or the like.

The network interface 150 may include one or more devices for enabling communication with other hardware devices. For example, the network interface 150 may include a network interface card (NIC) configured to communicate according to the Ethernet protocol. Additionally, the network interface 150 may implement a TCP/IP stack for communication according to the TCP/IP protocols. Various alternative or additional hardware or configurations for the network interface 150 will be apparent.

The network interface 150 may be in operable communication with one or more sensor devices 151. In the healthcare context, these may include sensors configured as part of patient monitoring devices that gather various types of information regarding a patient's health. For example, the one or more sensor devices 151 may include sensors used to conduct a radiology examination.

The type of sensor devices 151 used may of course vary and may depend on the patient, context, and the overall purpose of the medical examination. Accordingly, any type of sensor devices 151 may be used as long as they can gather or otherwise obtain the required data as part of an examination.

The sensor device(s) 151 may be in communication with the system 100 over one or more networks that may link the various components with various types of network connections. The network(s) may be comprised of, or may interface to, any one or more of the Internet, an intranet, a Personal Area Network (PAN), a Local Area Network (LAN), a Wide Area Network (WAN), a Metropolitan Area Network (MAN), a storage area network (SAN), a frame relay connection, an Advanced Intelligent Network (AIN) connection, a synchronous optical network (SONET) connection, a digital T1, T3, E1, or E3 line, a Digital Data Service (DDS) connection, a Digital Subscriber Line (DSL) connection, an Ethernet connection, an Integrated Services Digital Network (ISDN) line, a dial-up port such as a V.90, a V.34, or a V.34bis analog modem connection, a cable modem, an Asynchronous Transfer Mode (ATM) connection, a Fiber Distributed Data Interface (FDDI) connection, a Copper Distributed Data Interface (CDDI) connection, or an optical/DWDM network.

The network or networks may also comprise, include, or interface to any one or more of a Wireless Application Protocol (WAP) link, a Wi-Fi link, a microwave link, a General Packet Radio Service (GPRS) link, a Global System for Mobile Communication G(SM) link, a Code Division Multiple Access (CDMA) link, or a Time Division Multiple access (TDMA) link such as a cellular phone channel, a Global Positioning System (GPS) link, a cellular digital packet data (CDPD) link, a Research in Motion, Limited (RIM) duplex paging type device, a Bluetooth radio link, or an IEEE 802.11-based link.

The storage 160 may include one or more machine-readable storage media such as read-only memory (ROM), random-access memory (RAM), magnetic disk storage media, optical storage media, flash-memory devices, or similar storage media. In various embodiments, the storage 160 may store instructions for execution by the processor 120 or data upon which the processor 120 may operate.

For example, the storage 160 may include incidental finding extraction instructions 161, follow-up recommendation extraction instructions 162, association instructions 163 for associating follow-up recommendations with incidental findings, administrative guideline instructions 164, feature extraction and matching instructions 165, inconsistency determination instructions 166, user feedback instructions 167, and clinical care workflow instructions 168 for updating a clinical care workflow.

Figure 2:
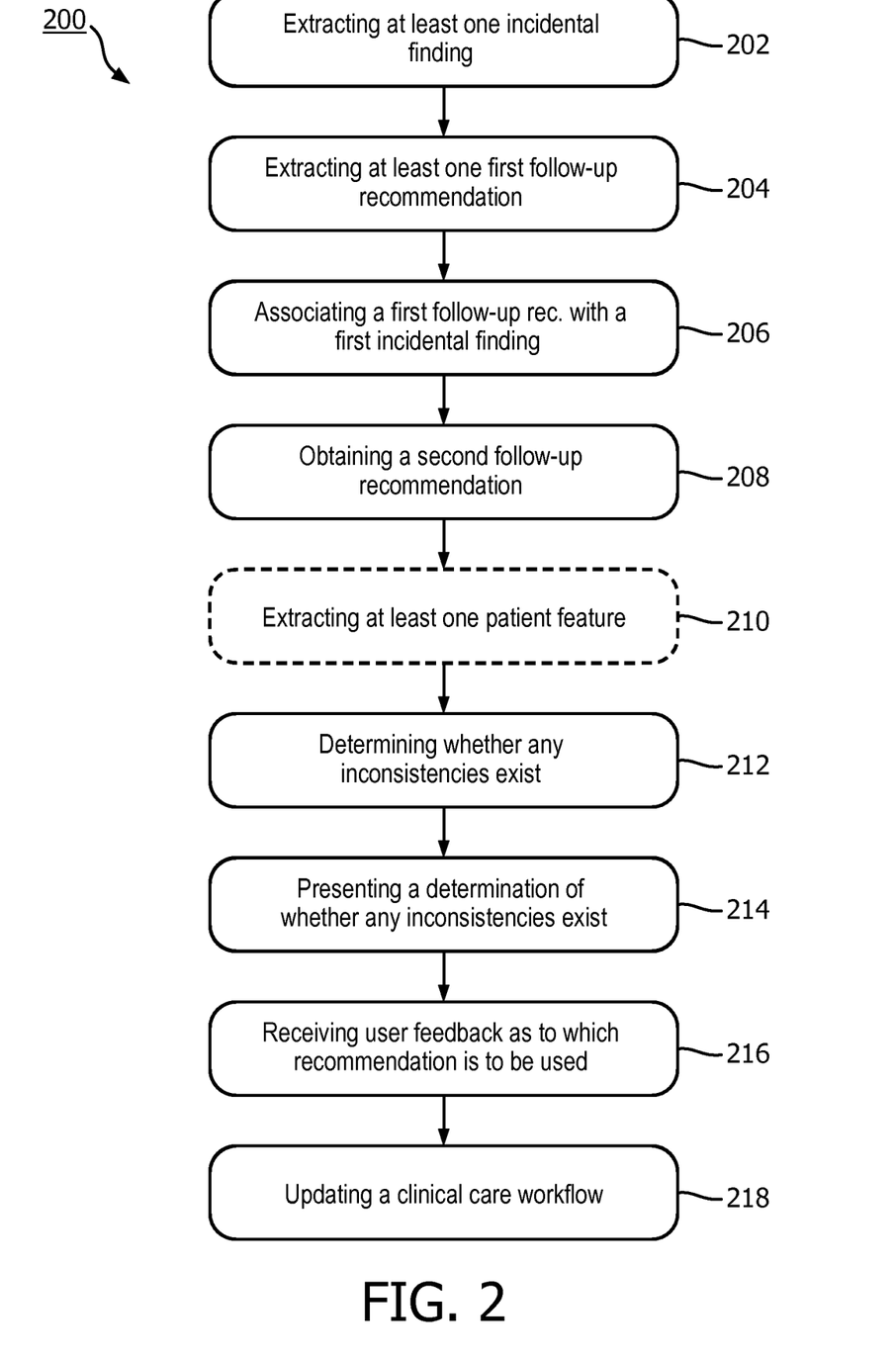
FIG. 2 depicts a flowchart of a method for selecting a treatment for a patient in accordance with one embodiment.

FIG. 2 depicts a flowchart of a method 200 for selecting a treatment for a patient in accordance with one embodiment. Method 200 may rely on the components of the system 100.

Step 202 involves extracting, using a processor executing instructions stored on a memory, at least one incidental finding from a record associated with the patient. The processor 120 may perform step 202 by executing the incidental finding extraction instructions 161.

The incidental finding extraction instructions 161 may cause the processor 120 to automatically identify and extract all incidental findings given the patient clinical history. These instructions 161 may specifically include identification instructions 169 and classification instructions 170. For example, the identification instructions 169 may be tasked with identifying certain words or other indicia in a patient's health record and may be executed by an engine consisting of Natural Language Processing (NLP) methods to extract findings based on certain ontologies, word2vec models, regular expressions, etc.

For example, findings of radiology examinations can be identified and labelled in sentences by keyword-matching using one or more of predefined dictionaries or existing ontologies. These ontologies may include, but are not limited to, SNOMED® and the Unified Medical Language System (UMLS).

Additionally or alternatively, the incidental findings can be identified and labelled in sentences by using regular expressions to match a pattern or by using previously-labelled data to train any type of appropriate machine learning model. The executed machine learning models may include, but are not limited to, support vector machines, random forests, recurrent neural networks, convolutional neural networks, or any other model that can classify findings from the report.

The identified findings are further analyzed to determine whether they are in fact incidental findings and not prior findings. In the context of the present application, the term "prior findings" may refer to findings that have been observed in prior studies or examinations of the same patient.

It is important for the instructions 161 to distinguish between incidental findings and prior findings as the appropriate workflow is different for these different types of findings. To distinguish between incidental findings and prior findings, the processor 120 may execute classification instructions 170 that rely on and use a list of keywords that accompany the incidental findings such as "new" or "incidentally found."

Similarly, the processor 120 may rely on and use a list of keywords that accompany prior findings such as "previously seen", "stable", "unchanged", or the like. Furthermore, the processor 120 may rely on one or more machine learning procedures such as support vector machines, random forests, recurrent neural networks, convolutional neural networks, or the like, to classify the findings.

In accordance with various embodiments, the identification task and/or the classification task may rely on an ensemble of the approaches described above. For example, the processor 120 may first run keyword matching to identify findings. To identify more challenging cases that are rare and not in the previously-defined dictionaries or ontologies (e.g., abbreviations that are not widely known), the processor 120 may train a machine learning model based on examples of such cases in order to identify the remaining findings that are not detected using keyword matching approaches.

Step 204 involves extracting, using the processor, at least one first follow-up recommendation from the record. The processor 120 may perform step 204 by executing the follow-up recommendation extraction instructions 162.

The follow-up recommendation extraction instructions 162 may enable the processor 120 to automatically detect and extract a follow-up recommendation in a patient health record such as in a clinical report. The follow-up recommendation extraction instructions 162 may include any suitable machine learning procedures and natural language processing techniques that look for specific keywords such as, but not limited to, "follow up" and "recommend." Additionally or alternatively, the processor 120 may rely on word2vec models trained on a corpus of annotated radiology reports.

This follow-up recommendation detection may be implemented as a machine learning problem, provided enough training examples. These machine learning techniques may include, but are not limited to, support vector machines, random forests, or even deep learning approaches such as recurrent neural networks and convolutional neural networks. Moreover, the processor 120 may execute an ensemble approach that combines keyword-based approaches and machine learning approaches.

Step 206 involves associating a first follow-up recommendation with a first incidental finding. The processor 120 may perform step 206 by executing the association instructions 163.

The association instructions 163 may link every incidental finding to a potential follow-up recommendation. The processor 120 may essentially look for proximity of the occurrence of an incidental finding and the follow-up recommendation phrase(s) and determine whether the follow-up recommendation phrase is related to the incidental finding. The processor 120 may perform this association step in one or more of three ways.

For example, the processor 120 may execute keyword-based association instructions 171. According to this technique, the processor 120 may determine the specific finding and the corresponding attributes of the finding in the follow-up recommendation. In radiology-based applications, attributes may include, but are not limited to, nodule size, nodule shape, nodule color, etc. The type of attribute considered may of course vary and may be based on the incidental finding. Then, the processor 120 may match the attributes to the sentence(s) describing the finding.

As another example, the processor 120 may execute correspondence instructions 172 to prepare paired training data consisting of a finding sentence and the corresponding follow-up sentence. The processor 120 may then provide the paired training data as input to train a machine learning/deep learning model to determine correspondence.

For example, the correspondence instructions 172 may rely on a recurrent neural network model to derive a feature representation for a finding sentence and a feature representation for a follow-up recommendation sentence. Then, the correspondence instructions 172 may rely on a second RNN to derive a co-occurrence feature representation for a finding-follow-up sentence pair.

As yet another example, the processor 120 may execute guideline-based instructions 173 for associating incidental findings with follow-up recommendations. For example, the processor 120 may rely on existing guidelines established by administrative bodies such as the Fleischner guidelines (discussed below) to determine which findings require which type of follow-up actions, and then look for a corresponding match in a report.

Step 208 involves obtaining, using an interface, a second follow-up recommendation from a third party-defined policy. The processor 120 may perform step 208 by executing the administrative guideline instructions 164.

The administrative guideline instructions 164 may enable the processor 120 to implement different guidelines for different types of incidental findings. For example, the administrative guideline instructions 164 may include instructions based on ACR guidelines 174 or other standardized guidelines, or instructions based on hospital-specific guidelines 175. These guidelines may be received by the network interface 150 from any appropriate location and/or may be stored in a database accessible by the system 100.

To implement these guidelines, the processor 120 may implement any type of rule-based framework such as if-then rules. Additionally or alternatively, the processor 120 may use a machine learning approach to train a model that, by providing a finding and corresponding attributes, can determine which guideline scenario matches best.

Step 210 involves extracting at least one patient feature from the electronic health record, wherein the at least one patient feature is required by the third party-defined policy, and the second follow-up recommendation is based on the at least one extracted patient feature. The processor 120 may perform step 210 by executing the feature extraction and matching instructions 165.

The processor 120 may execute the feature extraction and matching instructions 165 to extract features that are required based on the administrative guideline instructions 164. The processor 120 may extract these features from, for example, image and/or non-image data from the patient's record.

The features may be extracted from image data (e.g., DICOM® image data) and/or non-image data (EMR data, radiology reports, etc.). Different types of features may of course be extracted from both image and non-image data based on the requirements of the corresponding guidelines.

Figure 3:
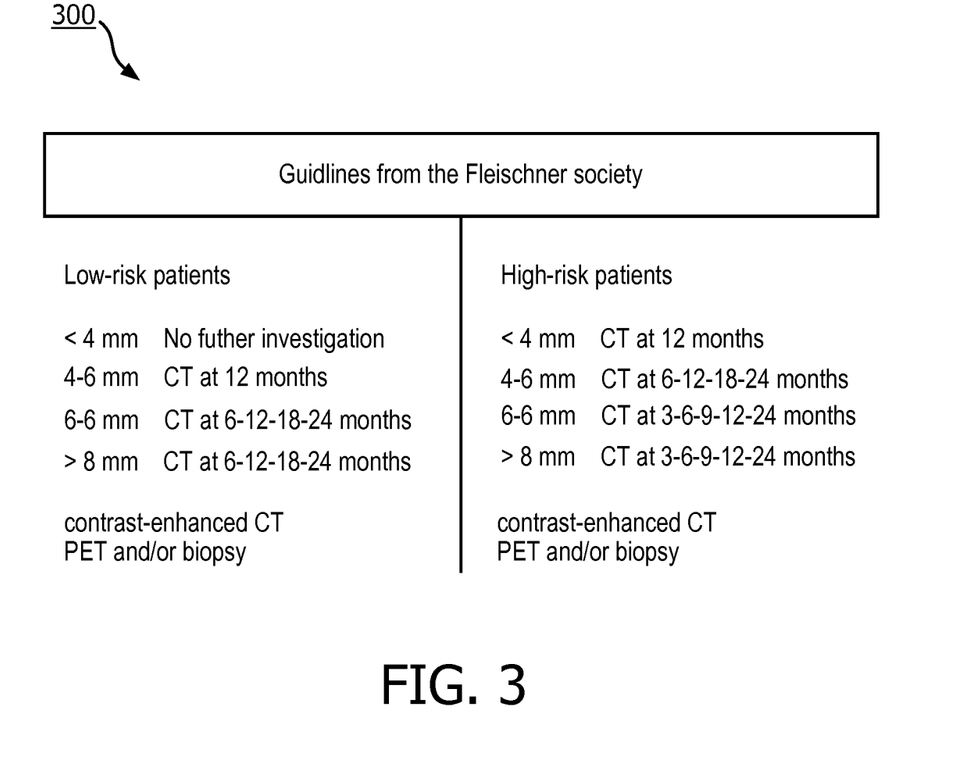
FIG. 3 illustrates exemplary follow-up recommendations based on institutional guidelines in accordance with one embodiment.

For example, FIG. 3 illustrates a table 300 showing exemplary guidelines based on the ACR guidelines 174. For lung cancer, the ACR guidelines are called "Fleischner" guidelines and the required features for extraction are nodule size, smoking history, etc.

As the guidelines often require information about the finding such as size, shape, color, etc., the processor 120 may extract attributes such as measurement, shapes, margin, or the like. For lung nodules specifically, the processor 120 may extract features such as solid/ground, glass/semi-solid, speculated, non-speculated, etc.

The instructions 165 for extracting these features may include instructions for extracting these features directly from the image data by using image processing approaches (e.g., segmentation, radiomics, etc.). Additionally or alternatively, attributes may be extracted from a corresponding radiology report by building keyword/regular expression matching methods and/or by training a machine learning model based on training data.

In the event the required features are not available, a clinician or the processor 120 may insert a plurality of ranges (e.g., all possible ranges) of a value for the missing values of the desired features to derive potential ranges of possibilities of outcome. The clinician may then make a decision based on the possible outcomes.

For example, the type of nodule is a feature required by the Fleischner Guidelines. The type of nodule may be classified ground-glass, sub-solid, or part-solid. If this information is not available, one can derive the suggested guideline for all three different types of values: Guideline_ground_glass, Guideline_part_solid, and Guideline_sub_solid.

The feature extraction and matching instructions 165 may then cause the processor 120 to analyze the extracted features to match the features with the administrative guidelines. The extracted features may be fed into an if-then framework, for example, to determine the appropriate follow-up recommendation according to the guidelines.

In order to determine an appropriate follow-up recommendation based on the Fleischner guidelines, the first step is to determine if the patient is a low risk patient or a high risk patient. This determination is based on the patient's age, sex, family history, smoking history, etc. This type of data can be automatically extracted from the patient's electronic medical record data.

Then, the ACR guidelines 174 may cause the processor 120 to extract the required data from the patient's record such as, but not necessarily limited to, nodule size and shape. This data may be extracted directly from an image using image processing techniques (e.g., segmentation) or from a patient's radiology report using NLP techniques. Additionally, and as discussed above, longitudinal data can be extracted from the history of the patient to determine the required longitudinal information such as nodule growth.

The feature extraction and matching instructions 165 may then cause the processor 120 to extract the follow-up sentence(s), word(s), phrase(s) (for simplicity, "sentence(s)") that are associated with the extracted feature(s). The features extraction and matching instructions 165 may then parse the follow-up sentence(s) to better understand the recommendation. Then, the feature extraction and matching instructions 165 may cause the processor 120 to determine the appropriate follow-up recommendation based on the selected guidelines (e.g., ACR guidelines, hospital guidelines, etc.).

Step 212 involves determining, using the processor, whether any inconsistencies exist between the first follow-up recommendation and the second follow-up recommendation. The processor 120 may perform step 212 by executing the inconsistency determination instructions 166.

The processor 120 may execute the inconsistency determination instructions 166 to determine whether any inconsistencies exist between the follow-up recommendations provided in the report (i.e., from step 204) and the follow-up recommendations provided by the guidelines (i.e., from step 208). For example, a follow-up recommendation from the report that reads "follow up CT imaging after 6 months" would be inconsistent with a follow-up recommendation from the guidelines that reads "follow up CT imaging after 12 months."

In another embodiment, the follow-up recommendation extracted from the report may not include all information that is required to form a "complete" recommendation. For instance, a radiologist may provide a follow-up recommendation in the patient's radiology report such as "a follow-up CT imaging is recommended." In this scenario, the radiologist forgot to include the timeframe in the recommendation.

In instances such as these, the inconsistency determination instructions 166 may compare the follow-up recommendation from the guidelines to the "partial" follow-up recommendation to determine the appropriate follow-up recommendation. The appropriate follow-up may be derived based on a maximum match (e.g., modality matching) between the guideline recommendation and the partial recommendation.

Step 214 involves presenting, using a user interface, a determination of whether any inconsistencies exist between the first follow-up recommendation and the second follow-up recommendation. The processor 120 may perform step 214 by executing the user feedback instructions 167.

For example, the processor 120 may present a message stating that the clinician's follow-up recommendation and the follow-up recommendation provided by the ACR are in agreement. Alternatively, the processor 120 may present a message warning of any inconsistencies between the follow-up recommendation from the report and the follow-up recommendation provided by, for example, the ACR. In some embodiments, such as the instances where only a "partial" follow-up recommendation is provided in the report, the user feedback instructions 167 may convey a message to a clinician to alert them about a partial match.

A clinician may review the presented information including the follow-up recommendation and the evidence supporting it, as well as specific image and/or non-image data from which required features were extracted. Furthermore, the clinician can access the reference sentence from where the follow-up recommendation is extracted.

Step 216 involves receiving, using the user interface, user feedback as to which recommendation is to be used to resolve any determined inconsistencies. The clinician may select the appropriate follow-up recommendation based on, for example, their knowledge, their past experience, the data supporting the recommended follow-up recommendations, or the like. In some embodiments, the clinician may be asked specifically to accept a follow-up recommendation or override a follow-up recommendation. The clinician may view the recommendations (as well as the evidence supporting the recommendations), and provide a response via a user interface such as the user interface 140 of FIG. 1.

Step 218 involves updating, using the processor, a clinical care workflow based at least on the received user feedback. The processor 120 may perform step 218 by executing the clinical care workflow instructions 168.

Once the clinician provides some indication with respect to the appropriate follow-up, the clinical care workflow instructions 168 may enable the processor 120 to prepare the clinical care workflow for the patient based on the selected follow-up. For example, the clinical care workflow instructions 168 may schedule an imaging, schedule a biopsy, report back to the appropriate clinician(s), report back to the patient, or the like.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

What is claimed is:

1. A computer-implemented method for selecting a treatment for a patient, the method comprising:
    extracting, using a processor executing instructions stored on a memory, at least one incidental finding from a record associated with the patient;
    extracting, using the processor, at least one first follow-up recommendation from the record;
    associating, using the processor, a first follow-up recommendation of the at least one first follow-up recommendation with a first incidental finding of the at least one incidental finding;
    obtaining, using an interface, a second follow-up recommendation from a third party-defined policy;
    determining, using the processor, an inconsistency exists between the first follow-up recommendation and the second follow-up recommendation, wherein the inconsistency identifies that the first follow-up recommendation is incomplete such that a clinical care workflow event of a clinical workflow that separately follows the first recommendation cannot be executed;
    presenting, using a user interface, the inconsistency between the first follow-up recommendation and the second follow-up recommendation;
    receiving, using the user interface, user feedback as to which recommendation is to be used to resolve any determined inconsistency; and
    updating, using the processor, the first follow-up recommendation with information to update and make the clinical care workflow event executable, wherein the clinical care workflow is separate from the follow-up recommendation and used for updating execution of a treatment based at least on the received user feedback, wherein the updating includes selecting the treatment for the patient, and wherein the clinical care workflow is implemented.

2. The method of claim 1 wherein the third party is at least one of a healthcare institution and an administrative body.

3. The method of claim 1 further comprising receiving, using the user interface, acceptance of one of the follow-up recommendations upon the processor determining an inconsistency exists between the first follow-up recommendation and the second follow-up recommendation.

4. The method of claim 1 wherein the at least one incidental finding relates to a finding of a radiology examination.

5. The method of claim 1 wherein extracting the at least one incidental finding includes:
    identifying the at least one incidental finding in a medical examination report, and
    confirming that the at least one incidental finding is not a prior finding by analyzing longitudinal data associated with the patient.

6. The method of claim 1 further comprising extracting at least one patient feature from an electronic health record, wherein the at least one patient feature is required by the third party-defined policy, wherein the second follow-up recommendation is based on the at least one extracted patient feature.

7. The method of claim 1 wherein associating the first follow-up recommendation with the first incidental finding includes using at least one of a keyword matching approach, a model trained on paired training data, and existing guidelines specifying a required incidental finding for a given follow-up recommendation.

8. The method of claim 1, wherein the clinical care workflow is a scheduling of a biopsy and the treatment includes conducting a biopsy.

9. The method of claim 1, wherein the user feedback selects the first follow-up recommendation.

10. The method of claim 1, further comprising:
    determining a follow up recommendation based on a comparison of the first follow-up recommendation, which is a partial follow-up recommendation, and the second follow-up recommendation.

11. The computer implemented method of claim 1, wherein the first follow-up recommendation is identified as incomplete because a time period in the first follow-up recommendation is missing.

12. The computer implemented method of claim 1, wherein the clinical workflow is scheduling and the clinical workflow event is an imaging examination or biopsy.

13. The computer implemented method of claim 1, wherein the method includes further treatment additional to the clinical workflow.

14. The computer implemented method of claim 1, wherein the first follow-up recommendation is a recommendation of a time period for scheduling an image examination or biopsy and the clinical care workflow is a scheduling workflow on a scheduling system.

15. A system for selecting a treatment for a patient, the system comprising:
    an interface for receiving a record associated with the patient; and
    a processor executing instructions stored on a memory to:
        extract at least one incidental finding from the record associated with the patient,
        extract at least one first follow-up recommendation from the record,
        associate the at least one first follow-up recommendation with the at least one incidental finding,
        obtain at least one second follow-up recommendation from a third party-defined policy,
        determine an inconsistency exists between the at least one first follow-up recommendation and the at least one second follow-up recommendation, wherein the inconsistency identifies that a clinical workflow event of a clinical workflow that separately follows the first recommendation cannot be executed, present, using a user interface, the inconsistency between the at least one first follow-up recommendation and the at least one second follow-up recommendation, receive, using the user interface, user feedback as to which recommendation is to be used to resolve any determined inconsistency, and update the clinical care workflow based at least on the received user feedback to make the clinical workflow event executable, wherein the updating includes selecting a treatment for the patient which is separate from the clinical care workflow, and wherein the clinical care workflow is implemented.

16. The system of claim 15 wherein the third party is at least one of a healthcare institution and an administrative body.

17. The system of claim 15 wherein the user interface is further configured to receive acceptance of one of the follow-up recommendations upon the processor determining an inconsistency exists between the at least one first follow-up recommendation and the at least one second follow-up recommendation.

18. The system of claim 15 wherein the at least one incidental finding relates to a finding of a radiology examination.

19. The system of claim 15 wherein the processor is configured to extract the at least one incidental finding by:
   identifying the at least one incidental finding in a medical examination report, and
   confirming that the at least one incidental finding is not a prior finding by analyzing longitudinal data associated with the patient.

20. The system of claim 15 wherein the processor is further configured to extract at least one patient feature from an electronic health record, wherein the at least one patient feature is required by the third party-defined policy, wherein the second follow-up recommendation is based on the at least one extracted patient feature.

21. The system of claim 15 wherein the processor associates the at least one first follow-up recommendation with the at least one incidental finding using at least one of a keyword matching approach, a model trained on paired training data, and existing guidelines specifying a required incidental finding for a given follow-up recommendation.

22. A non-transitory computer-readable medium containing computer executable instructions for performing a method for selecting a treatment for a patient, the computer-readable medium comprising:
   computer-executable instructions for extracting, using a processor executing instructions stored on a memory, at least one incidental finding from a record associated with the patient;
   computer-executable instructions for extracting, using the processor, at least one first follow-up recommendation from the record;
   computer-executable instructions for associating the at least one first follow-up recommendation with the at least one incidental finding;
   computer-executable instructions for obtaining, using an interface, at least one second follow-up recommendation from a third party-defined policy;
   computer-executable instructions for determining, using the processor, whether any inconsistency exists between the at least one first follow-up recommendation and the at least one second follow-up recommendation;
   computer-executable instructions for presenting, using a user interface, a determination of whether an inconsistency exists between the at least one first follow-up recommendation and the at least one second follow-up recommendation;
   computer-executable instructions for receiving, using the user interface, user feedback as to which recommendation is to be used to resolve any determined inconsistency; and
   computer-executable instructions for updating, using the processor, a clinical care workflow based at least on the received user feedback, and
   computer-executable instructions for deriving the follow-up recommendation based on a modality matching between the second follow-up recommendation and the first follow-up recommendation,
   wherein the updating includes selecting a treatment for the patient, and wherein the clinical care workflow is implemented.

* * * * *